(12) United States Patent
Pardini et al.

(10) Patent No.: US 12,165,320 B2
(45) Date of Patent: Dec. 10, 2024

(54) OPTICAL MAMMOGRAPH USING NEAR-INFRARED IN DIFFUSE REFLECTANCE GEOMETRY

(71) Applicants: CONSEJO NACIONAL DE INVESTIGACIONES CIENTÍFICAS Y TÉCNICAS (CONICET), Ciudad Autónoma de Buenos Aires (AR); Pamela Alejandra Pardini, San Carlos de Bariloche (AR)

(72) Inventors: Pamela A. Pardini, Prov. de Río Negro (AR); Héctor A. García, Prov. de Buenos Aires (AR); María V. Waks Serra, Prov. de Buenos Aires (AR); Nicolás A. Carbone, Prov. de Buenos Aires (AR); Daniela I. Iriarte, Prov. de Buenos Aires (AR); Guido R. Baez, Prov. de Buenos Aires (AR); Hector O. Di Rocco, Prov. de Buenos Aires (AR); Juan A. Pomarico, Prov. de Buenos Aires (AR)

(73) Assignees: CONSEJO NACIONAL DE INVESTIGACIONES CIENTÍFICAS Y TÉCNICAS (CONICET), Buenos Aires (AR); Pamela Pardini, San Carlos de Bariloche (AR)

( * ) Notice: Subject to any disclaimer, the term of this patent is extended or adjusted under 35 U.S.C. 154(b) by 182 days.

(21) Appl. No.: 17/415,553

(22) PCT Filed: Dec. 16, 2019

(86) PCT No.: PCT/IB2019/060862
§ 371 (c)(1),
(2) Date: Jun. 17, 2021

(87) PCT Pub. No.: WO2020/128795
PCT Pub. Date: Jun. 25, 2020

(65) Prior Publication Data
US 2022/0058802 A1 Feb. 24, 2022

(30) Foreign Application Priority Data
Dec. 17, 2018 (AR) .............................. 20180103682

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/0077* (2013.01); *A61B 5/0091* (2013.01);
(Continued)

(58) Field of Classification Search
CPC ......... G06T 7/0014; G06T 7/74; G06T 7/337; G06T 2207/30068; H04N 23/80;
(Continued)

(56) References Cited

U.S. PATENT DOCUMENTS 6,665,557 B1 12/2003 Alfano et al.
7,397,943 B2 * 7/2008 Merbach ............ G06V 40/1312
 348/42
(Continued)

FOREIGN PATENT DOCUMENTS

WO WO2018132908 A1 7/2018

OTHER PUBLICATIONS

Nicolás Abel Carbone; Doctoral Thesis, "Estudio de formación de imágenes en geometrías de reflectancia usando luz de onda continua en el infrarrojo cercano—Aplicación a la mamografía" doctoral thesis defense; Tesis Para Optar Por El Grado De Doctor En Ciencias Físicas; Dec. 18, 2017; pp. 1-205.

*Primary Examiner* — James T Boylan
(74) *Attorney, Agent, or Firm* — The Roy Gross Law Firm, LLC; Roy Gross

(57) ABSTRACT

A mammographic imaging device for analysis and detection of possible inhomogeneities in breast tissue of a patient using laser light in the near-infrared in diffuse reflectance geometry, includes a patient horizontal support comprising at least one transparent window in its cross-section and a measuring mechanism below the at least one transparent window and carried by said support. The measuring mechanism includes a laser-light producing mechanism for producing laser light beams in the near-infrared, a directing mechanism for directing said laser light beams towards the at least one transparent window, at least one wavelength filter, a light-sensing and imaging mechanism for sensing light and producing images and a controlling, processing and image-normalizing unit for controlling, processing and normalizing images.

18 Claims, 4 Drawing Sheets

(51) Int. Cl.
*G06T 7/33* (2017.01)
*G06T 7/73* (2017.01)
*H04N 23/56* (2023.01)
*H04N 23/75* (2023.01)
*H04N 23/80* (2023.01)

(52) U.S. Cl.
CPC ............ *A61B 5/7203* (2013.01); *G06T 7/337* (2017.01); *G06T 7/74* (2017.01); *H04N 23/56* (2023.01); *H04N 23/75* (2023.01); *H04N 23/80* (2023.01); *G06T 2207/30068* (2013.01)

(58) Field of Classification Search
CPC ...... H04N 23/56; H04N 23/75; A61B 5/0077; A61B 5/0091; A61B 5/7203
See application file for complete search history.

(56) References Cited

U.S. PATENT DOCUMENTS

| | | | |
|---|---|---|---|
| 2002/0045833 A1 | 4/2002 | Wake et al. | |
| 2004/0030255 A1 | 2/2004 | Alfano et al. | |
| 2004/0097811 A1* | 5/2004 | Smith | A61B 5/4312 600/448 |
| 2009/0080604 A1* | 3/2009 | Shores | A61B 6/487 378/37 |
| 2010/0074399 A1* | 3/2010 | Majewski | G01T 1/00 250/363.02 |
| 2011/0170107 A1* | 7/2011 | Hagen | A61B 5/0091 356/451 |
| 2012/0302865 A1* | 11/2012 | Tokita | A61B 5/4312 600/407 |
| 2012/0326055 A1* | 12/2012 | Wilson | A61B 5/0059 250/459.1 |
| 2015/0355443 A1* | 12/2015 | Okabe | G02B 21/367 348/80 |
| 2015/0362427 A1* | 12/2015 | Novotny | G01J 3/433 356/39 |
| 2016/0139039 A1 | 5/2016 | Ikehara et al. | |
| 2017/0078584 A1 | 3/2017 | Won | |
| 2019/0307334 A1* | 10/2019 | Wang | A61B 5/0095 |
| 2020/0060548 A1* | 2/2020 | Gomez | A61B 5/0086 |
| 2020/0178781 A1* | 6/2020 | Tabata | A61B 1/063 |
| 2020/0408701 A1* | 12/2020 | Nakamura | G01N 21/9505 |
| 2022/0323043 A1* | 10/2022 | Duric | A61B 5/4836 |

\* cited by examiner

OPTICAL MAMMOGRAPH USING NEAR-INFRARED IN DIFFUSE REFLECTANCE GEOMETRY

FIELD OF THE INVENTION

This invention relates to a mammographic imaging device for analysis and detection of possible inhomogeneities in breast tissue that may be caused by different neoplastic pathologies, using near-infrared laser in diffuse reflectance geometry.

BACKGROUND OF THE INVENTION

It is well known that mammographies may save lives if breast cancer is detected early on. For this purpose, there exist several devices for analyzing breast tissue and detecting inhomogeneities, should there be any.

The main drawback of known devices used for mammographies is that they present a relatively low specificity and low sensitivity. Normal breast tissue may hide a tumor, which may not be perceived by such devices, which provides a diagnosis described as a false negative (low sensitivity). Furthermore, these devices may identify some abnormality that may seem to be a tumor but that may end up not being one, which is described as a false positive (low specificity).

Devices most widely used nowadays for detecting inhomogeneities in breast tissue or mammographies use x ray ionizing radiation, which prevents the continued use of said devices for monitoring evolution of disease due to radiation exposition. Furthermore, said devises usually imply patient's breasts being compressed, which is quite a traumatic experience for patients in general.

Due to the above, alternative devices to those traditionally used have been developed, such as those that use radiation with infrared wavelengths. This kind of device allow for better disease monitoring, as well as regular checkups as frequently as the medical practitioner considers it necessary, since infrared radiation is non-ionizing and, thus, poses no risks for patients. Said devices that employ infrared light may further be used in situations where X-rays are not recommended, for example for continuous monitoring, assessment of pregnant women, etc.

There exist several devices in the current state of the art that employ infrared light or radiation, among those, the device described in U.S. patent application 2002/045833 A1, directed to a diagnostic medical imaging device and, in particular, to a mammograph using a near-infrared laser as radiation source. Said apparatus consists of a CCD sensors array disposed in the form of a ring wherein one line of measurements is taken at a time for each position of the ring; this means that it does not involve full-field imaging but a series of data that must be appropriately processed in order to rebuild an image.

Additionally, patent application WO 2018/132908 A1 is directed to a handheld device for scanning human tissue through diffusion optical spectroscopy that comprises means for emitting electromagnetic radiation at one or more wavelengths corresponding to absorption associated with one or more human-tissue constituents, means for detecting electromagnetic radiation and processing means for producing, in response to the received electromagnetic radiation, one or more images of the human tissue. However, linear CCD arrangements that measure luminous intensity line to line are used, besides being a slow process (limited by the speed at which the measuring head may be manually moved), subject to operation errors. Furthermore, this device does not produce a full 2D-image of the area to be explored in just one use.

Finally, U.S. patent application 2016/0139039 A1 is directed to an imaging system that includes an infrared camera that is sensitive to light of wavelengths in the near-infrared region, a lighting unit that emits light beams having multiple wavelength in an infrared region that includes the wavelengths to which the infrared camera is sensitive, and a control unit that controls capture of an image by the infrared camera and emission of a light beam by the lighting unit. However, large LED sources are used in this device, which prevents the obtention of in-depth information and only registers a map of the surface. Moreover, in the case of breasts, compression between plates is required.

Therefore, there is a need for a device that avoids compression of the breast to be analyzed, and thus the traumatic situation associated thereto, so as to substantially improve patient comfort, and that allows for the production of full-field images of the area to be analyzed, at a high speed.

BRIEF DESCRIPTION OF THE INVENTION

Based on the foregoing, this invention provides a mammographic imaging device that allows taking full-field images of the area to be analyzed and does not involve breast compression, using diffuse reflectance geometry and thus overcoming the problems mentioned above.

For the purposes of this invention, expressions "laser light", "light beams", "laser light beams", "NIR light", "NIR light beams" and variations thereof will be used interchangeably, meaning in all cases coherent light beams emitted with near-infrared wavelength.

Therefore, the object of this invention is a mammographic imaging device for analysis and detection of possible inhomogeneities in breast tissue of a patient using laser light in the near-infrared in diffuse reflectance geometry, wherein said device comprises:

a patient horizontal support comprising at least one transparent window in its cross-section;

measuring means below the at least one transparent window and carried by said support, wherein said measuring means comprise:

laser-light producing means for producing laser light beams in the near-infrared;

light-directing means for directing said laser light beams towards the at least one transparent window;

at least one wavelength filter;

light-sensing and imaging means for sensing light and producing images; and an image controlling, processing and normalizing unit for controlling, processing and normalizing images.

In a preferred embodiment of the present invention, the support is a stretcher wherein the patient lies in decubito prono position.

In a preferred embodiment of the present invention, the at least one window is made from a transparent material.

In a preferred embodiment of the present invention, the at least one window presents flat and parallel upper and bottom surfaces.

In a preferred embodiment of the present invention, the at least one window is made of glass or a transparent polymer.

In a preferred embodiment of the present invention, light-regulating means are placed below the at least one window and attached to the support.

In an even more preferred embodiment of the present invention, the light-regulating means comprise a diaphragm.

In a preferred embodiment of the present invention, the laser-light producing means in the near-infrared comprise at least two laser light producers of different wavelengths.

In an even more preferred embodiment of the present invention, two laser light producers are used, placed so that the laser light beams produced are perpendicular to one another.

In an even more preferred embodiment of the present invention, a beam divider is placed so that said beams perpendicular to one another incide collinearly on the light-directing means.

In an even more preferred embodiment of the present invention, light-intensity regulating means for regulating the intensity of laser light beams are placed, preferably a variable attenuator, in front of each of the laser-light producing means.

In a preferred embodiment of the present invention, the light-directing means comprise a galvanometric scanner.

In a preferred embodiment of the present invention, the at least one wavelength filter is an interferometric filter.

In a preferred embodiment of the present invention, the light-sensing and imaging means comprise a high-sensitivity CCD camera that takes a full-field image.

In an even more preferred embodiment of the present invention, the high-sensitivity CCD camera is a 2D CCD camera.

In an even more preferred embodiment of the present invention, a cover for isolating ambient light is disposed between the at least one transparent window and the light-sensing and imaging means.

In a preferred embodiment of the present invention, the image controlling, processing and normalizing unit:
a) eliminates noise from images produced by the light-sensing and imaging means;
b) determines the position of the light beams and clips an area of interest around the same;
c) creates a reference image with clippings;
d) normalizes clippings using the reference image; and
e) rebuilds images repositioning the normalized clippings.

DETAILED DESCRIPTION OF THE INVENTION

The present invention will be described in further detail below, with reference to the accompanying figures that illustrate exemplary embodiments of the invention, which must not be interpreted as limiting.

The same reference numbers are used in each figure for each element of the device of the invention.

Figure 1:
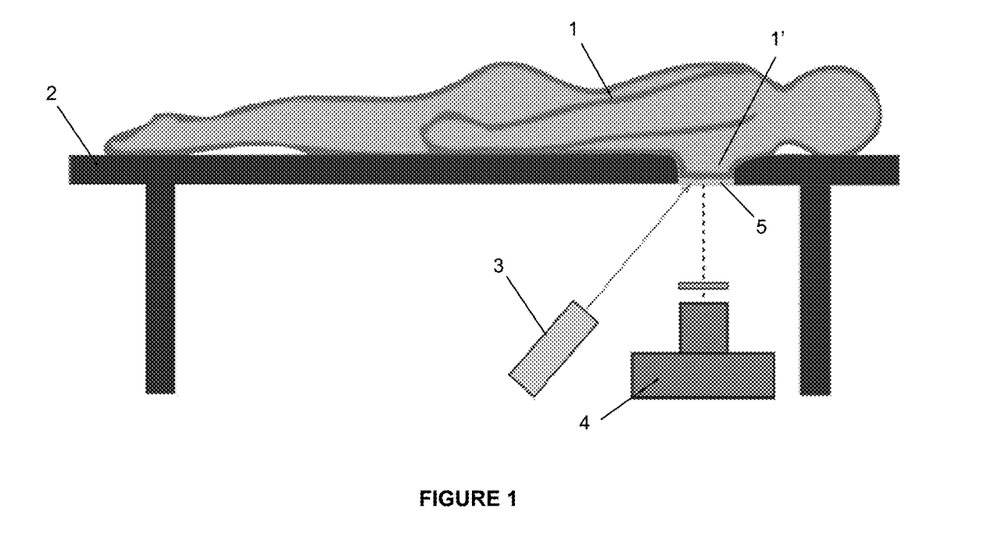
FIG. 1 is a simplified schematic view of the device of the present invention.

FIG. 1 shows a simplified schematic view of an embodiment of the device of the present invention, wherein a patient 1 and her breasts 1', a stretcher 2, laser-light producing means 3 for producing laser light beams, light-sensing and imaging means 4 for sensing light and producing images and a transparent window 5 can be observed.

In said FIG. 1, the patient 1 can be observed in a decubito prono position on the stretcher 2 having her breasts resting on the transparent window 5. The use of the transparent window 5 avoids compression of the breast between two plates, which is typical of traditional mammographic devices, and patient 1 comfort is substantially improved since the only compression on her breasts 1' comes from the patient's 1 own bodyweight. The transparent window 5 has two flat surfaces, an upper surface and a bottom surface, parallel and opposite to one another. Moreover, said window 5 helps to provide a flat surface of the breast to be analyzed, which aids in improving the resolution of a 2D image of the areas of interest of the breasts, as the surface of the breast 1' lies flat when resting on the upper surface of the window 5, thus making it unnecessary to perform any corrections due to the curvature of the breast's 1' surface.

Additionally, measuring means below the stretcher 2 that comprise laser-light producing means 3 and light-sensing and imaging means 4 are shown in a very simplified manner. Said laser-light producing means 3 and light-sensing and imaging means 4 comprise, respectively, laser light producers, which emit in the near-infrared, and a 2D or bi-dimensional CCD camera which enables taking full-field images, that is, it makes it possible to produce an image of the whole surface to be analyzed in just one take. Said means are positioned in diffuse reflectance geometry, thus, the phenomenon by which the device of the present invention operates is light reflectance, that is, light enters through the same face through which it exits. These laser-light producing means 3 and light-sensing and imaging means 4 will be described in greater detail below, along with FIG. 2.

Figure 2:
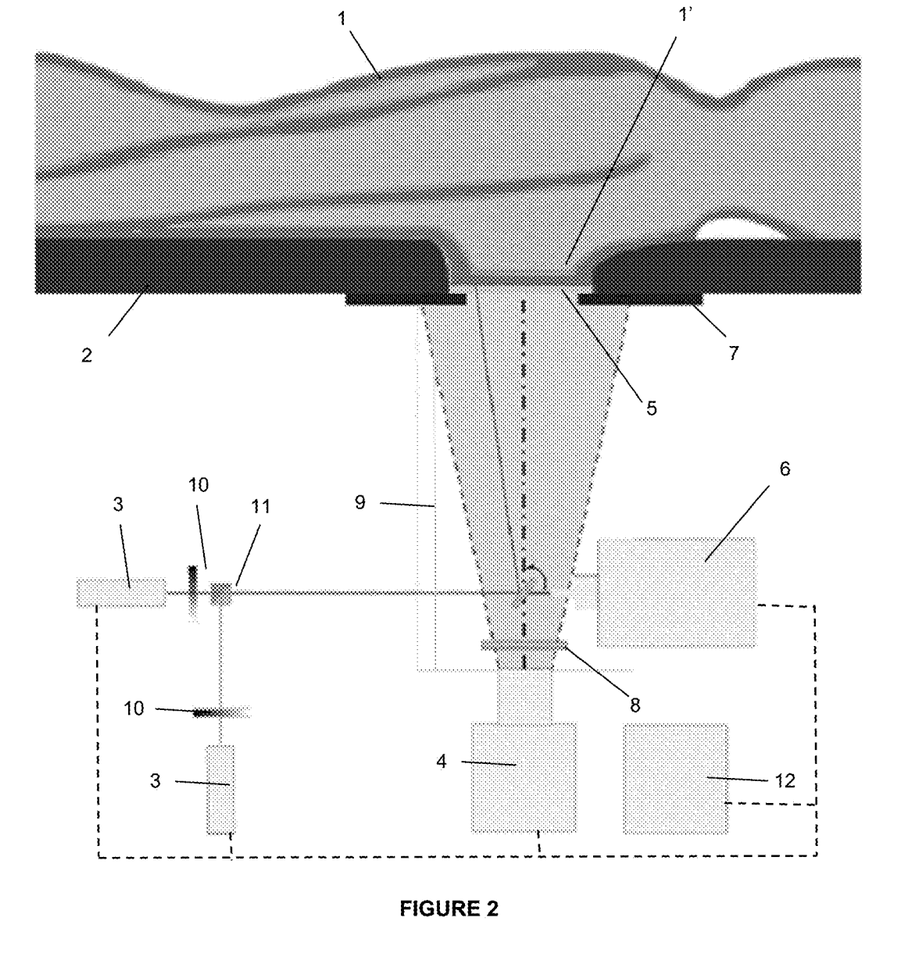
FIG. 2 is a detailed schematic view of the device of the present invention.

FIG. 2 shows a detailed schematic view of the device of the present invention which comprises laser-light producing means 3, light-sensing and imaging means 4, a transparent window 5, light-directing means 6 for directing said light beams, light-regulating means 7, a wavelength filter 8, a cover 9, two variable attenuators 10 as light-intensity regulating means for regulating the intensity of light beams, a light-beam divider 11 and an image controlling, processing and normalizing unit 12 for controlling, processing and normalizing images.

The laser-light producing means 3 comprise two laser light producers that emit coherent light beams (shown in continuous lines in FIGS. 2 and 3) in different wavelengths within the wavelength interval corresponding to near-infrared (NIR). Said laser light producers are positioned so that NIR light beams are perpendicular to one another and operate independently and sequentially. It should be mentioned that two laser light producers are used, with different near-infrared wavelengths so as to distinguish, in the obtained images, the differential absorption between oxyhemoglobin and deoxyhemoglobin, which have absorption peaks at said different wavelengths. This generates an oxygen saturation may through a technique known as differential optical absorption spectroscopy (DOAS). This is particularly important from a diagnosis point of view, since oxygen saturation distribution is a differentiating factor between malignant and benign tumors. Generally, benign tumors have homogeneous oxygen saturation on their surface, while malignant tumors have a hypoxic zone in their oxygenless center.

The light-sensing and imaging means 4 comprise a high-sensitivity CCD camera, preferably a 2D CCD camera. Said CCD camera incorporates an optic which allows measuring lightning intensity of the full 2D surface of the breast 1', when the patient 1 is in decubito prono position, as a single photograph of the NIR light reflected by each position of the laser light beam. It should be mentioned that it is not possible to perform this with a lineal arrangement of CCD cameras or sensors, as it is necessary to scan the complete area, capturing line by line. That is, the main advantage of using a 2D CCD with image production optics is that the complete area of interest is measured in only one take per laser position. It is even possible to take multiple images of each position in quick succession so as to improve the dynamic range with a high dynamic range (HDR) algorithm and improve the signal-noise ratio. Said camera may also make up for the position and the size of the breast resting on the transparent window 5.

A variable attenuator 10 is positioned in front of each of the laser-light producing means 3, reducing the intensity of said light beams as necessary in order to regulate the intensity of the laser light that incides on the breast 1' of the patient 1 and make up for the different relative absorptions, so as not to saturate the camera detectors. As mentioned above, said laser-light producing means 3 are positioned so that the light beams, with near-infrared wavelength, are perpendicular to one another and operate sequentially and independently, that is, one of them incides first, and then the other one. In order to ensure that said light beams incide on the same point or area of the transparent window 5, and thus of the breast 1', so that images produced by the 2D CCD camera are not offset in respect to one another, a light beam divider is placed, which makes the beams incide collinearly on the light-directing means 6. Said light-directing means 6 comprise a galvanometric scanner that directs the NIR light beams, independently, towards the same area on the transparent window 5 and scans the area to be analyzed. Said galvanometric scanner comprises a positioning system that allows the area of incidence of the produced light beams to be changed, which is also the only movable part of the device of the present invention. Two images are taken with the 2D CCD camera per each position of the scanner, one for each laser light of different wavelength, to then change to a new position, take the corresponding images and so on until the complete area to be analyzed is covered Light-regulating means 7 are mounted to the stretcher 2 and positioned below the transparent window 5, said means comprising a diaphragm capable of regulating the amount of light that enters into the window 5 so as to incide on the area of interest of the breast V and that exists said window 5, due to light reflection, so as to be received by the 2D CCD camera.

The NIR light directed by the galvanometric scanner incides on the area of interest of the breast 1', one part of it being reflected and the other part being propagated into the breast 1'. Propagation of NIR light upon finding any possible inhomogeneity within the breast 1', whether a tumor or a cyst, will be affected when exiting the breast 1' due to transport within said inhomogeneity. If the inhomogeneity is more absorbent, as may be a tumor, a lower-intensity light will exit said breast 1' due to additional absorption by said inhomogeneity. If the inhomogeneity is less absorbent, as may be a cyst, light will exit said breast 1' with a higher intensity. This behaviour of intensity of the reflected light beams is expected as tumors are more absorbent since, due to neovascularization, they have a higher blood supply, which makes them darker. On the contrary, cysts are almost translucent, and infrared light can easily go through them.

As propagation of the NIR light when it enters the breast 1' is not in a straight line but diffusely, because of several dispersion processes, the severe drop of intensity of the reflected light as it moves away from the source, and the noisy nature of the images, subtle variations in images due to the presence of possible inhomogeneities in breast tissue may be difficult to perceive. Moreover, said possible inhomogeneities may have optic properties that do not differ greatly from those of the surrounding environment, thus making the inhomogeneities more difficult to detect. In order to solve the above issues, it is possible to apply several fluorescent and/or absorbent markers that bind specifically to tumors, as indocyanine green (ICG) and gold nanoparticles (GNR).

Prior to being received by 2D CCD camera, reflected light goes through a wavelength filter 8, which is an interferometric filter that enables selection of determined wavelengths, useful in the optic characterization of the analyzed breast tissue so as to improve the resolution of the images produced by the CCD camera. It should be highlighted that a cover for isolating ambient light is placed between the transparent window 5 and said CCD camera, so that ambient light does not affect image capturing and does not hinder the detection of inhomogeneities in breast tissue.

The image controlling, processing and normalizing unit 12 for controlling, processing and normalizing the images is connected (dashed line in FIGS. 2 and 3), whether through a wire or wirelessly, to the two laser light producers, the galvanometric scanner and the 2D CCD camera, so as to control each of them. In order to process, normalize and rebuild images obtained by the 2D CCD camera, said unit 12 carries out a method comprising different steps. In a first step, noise is eliminated from the obtained images using a background image that accounts for ambient noise and noise from CCD electronics. In a second stage, the position of the NIR light beam is determined for each image, and an area is clipped around the same, so that the incident source or NIR light beam is always placed at the center of the area being photographed. Each individual image obtained in the corresponding clipping is smaller than the analyzed area, and a step size is determined so that translation is less than the image of the individual images, in order to obtain some overlap that aids in the final rebuilding and the noise reduction. In a third stage, since the source is always located at the center of each image, and it is expected that hypothetical inhomogeneities may be in different positions in each image, an average image is generated with each of the clippings obtained in the previous stage, wherein the presence of possible inhomogeneities is blurred. Said average image serves as reference for normalization. In a fourth stage, each of the clippings is normalized using the average image from the previous stage. This normalization is needed to homogenize exposure of the complete explored area and highlight the presence of possible inhomogeneities. In a fifth and last stage, the normalized, clipped images are repositioned to their original position, rebuilding a normalized full-field image where the presence of inhomogeneities may be assessed and tumor and cyst areas may be distinguished from the rest of the healthy tissue of the tissue being analyzed.

The set of characteristics described so far imply that full-field measurements may be taken in a quick and simple mechanical way, being the galvanometric scanner, responsible for repositioning the laser light source, the only movable part of the system. The CCD camera and the optic arrangement for producing images are completely static. As a result, data obtention takes up a very short period of time, about a few seconds per position and not more than 5 to 10 minutes for complete taking. Thanks to the image controlling, processing and normalizing unit 12, a topological image of the concentration of oxy/deoxyhemoglobin and/or contrast medium, which can be directly interpreted by a medical practitioner, is obtained. Said image can be repeated as many times as the medical practitioner deems it necessary, as infrared radiation does not pose any risks for the patient and there is no influence of it over the device; thus, it is possible to reduce the amount of false positive results, typical of traditionally employed mammographs. Furthermore, with the device of the present invention, there is no need for the safety infrastructure which is essential for X-ray facilities, which lowers costs considerably. The whole measurement system is self-contained under the stretcher and, due to the proposed geometry; breast compression is avoided thanks to the use of the transparent window, which is more comfortable and less traumatic for patients.

Figure 3:
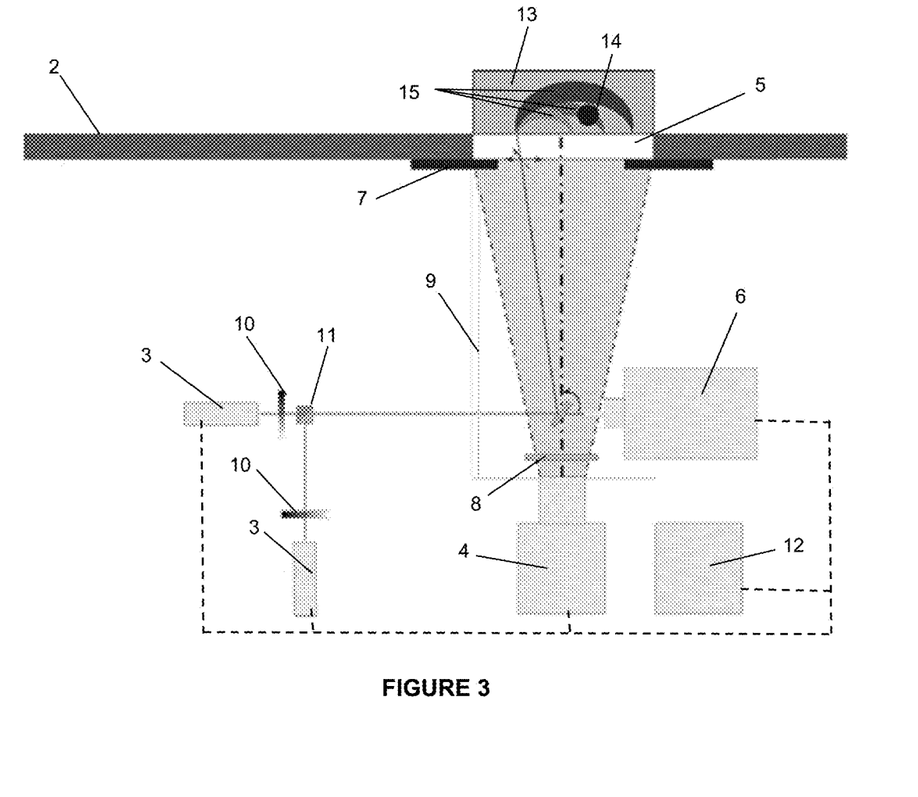
FIG. 3 is a detailed schematic view of the device of the present invention applied to phantoms.

FIG. 3 shows a schematic view of the several components of the embodiment of FIG. 2 applied to a test with a phantom 13 that has an inclusion 14 and photon propagation areas 15.

Phantoms are artificial means that emulate the optic properties of biological tissues, for example breast tissue. The phantom 13 shown in FIG. 3 presents an inclusion 14 or foreign object and areas 15 with a banana- or half-moon-shaped profile, that represent the most likely paths of the light within the medium, based on the position of the source (chosen by the positioning system of the galvanometric scanner) and the exit point (a pixel in the 2D image produced by the CCD camera). As mentioned above with reference to the propagation of the NIR light upon encountering an absorbent object, in this case, the inclusion 14 within the phantom 13, will affect propagation of light within banana-shaped areas 15 that go through it. As a consequence, the light that exits the medium will be less intense in the pixels that will make up the images of the final spot of those banana-shaped areas. On the other hand, a fluorescent object, besides behaving as an absorbent object, will reemit light at a different wavelength.

The areas 15 with a banana-shaped profile that are affected by the inclusion 14 depend on the position of such inclusion, both on the xy plane, which is parallel to the transparent window 5, and in depth z, which is a direction orthogonal to said xy plane, and the position of the incident source or NIR light beam. This dependence may thus be used to infer the position of the inclusion in the 3D space. Accordingly, full-field reflectance may provide primary depth-information.

EXPERIMENTAL RESULTS

Figure 4:
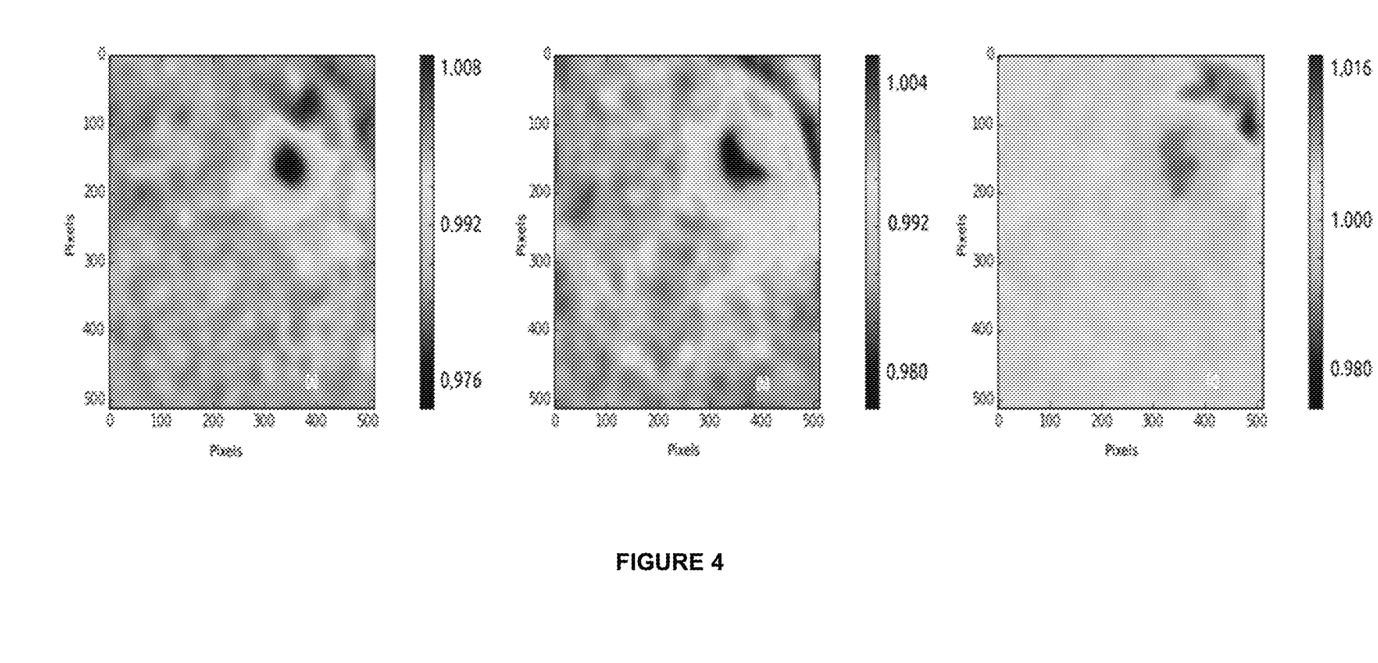
FIG. 4 shows experimental results applied to phantoms using the arrangement of FIG. 3.

FIG. 4 shows experimental results obtained after normalization, described above, of images obtained from phantoms using the arrangement of FIG. 3 and only one position of the source. Said FIG. 4 shows normalized absorption images from three different phantoms having an inclusion located 2.1 cm from the source in the xy plane but at three different analyzed depths: (a) z=1.35 cm, (b) z=1.55 cm and (c) z=1.75 cm.

It may be observed that while contrast (modulation) is low, presence of inclusion is seen unambiguously up to, at least, a depth z=1.75 cm. It is important to mention that the signal in the image corresponding to the inclusion is well located and defined. As expected, the signal-noise ratio decreases as depths increases. However, it should be highlighted that in these images, the apparent size and the location of the inclusion is mostly kept constant. In said FIG. 4, values of about 1, in the intensity color scale normalized next to each image, imply that there is no difference with homogeneous tissue. On the other hand, areas with a modulation lower than 1 mean that less photons reached the detector than would have if the medium was homogeneous, which reveals the presence of an inclusion more absorbent than the phantom's homogeneous tissue.

The invention claimed is:

1. A mammographic imaging device for analysis and detection of possible inhomogeneities in breast tissue of a patient using laser light in the near-infrared (NIR) in diffuse reflectance geometry by:
    (i) capturing images of breast tissue and
    (ii) analyzing said captured images to detect possible inhomogeneities in breast tissue;
    wherein said mammographic imaging device comprises a patient horizontal support comprising at least one transparent window and measuring means placed below the at least one transparent window and carried by said patient horizontal support, said measuring means comprising:
    (a) at least two laser-light producing means for producing laser light beams in the near-infrared;
    (b) light-directing means for directing said laser light beams towards the at least one transparent window;
    (c) at least one wavelength filter; light-sensing and imaging means for sensing light and producing images; and
    (d) an image controlling, processing and normalizing unit for controlling, processing and normalizing images, said unit performs multiple-step image processing including
        (i) eliminating noise from images produced by the light-sensing and imaging means;
        (ii) determining NIR light beam's position and clips said position to select it and ensure that the NIR light beam always remains at the same position at the center of each image;
        (iii) creating an average image of the multiple clipped images
        (iv) normalizing each clipped image using said average image of step (iii) to mitigate the impact of the variations and irregularities present in individual images and to standardize the exposure of the images across the entire analyzed area; and
        (v) repositioning said normalized clipped images of step (iv) to their original positions and combines them to reconstruct a full-field image that has been normalized
    further wherein said mammographic imaging device allows taking full-field images of the breast tissue area to be analyzed while avoiding compression of the breast between plates.

2. The device according to claim 1, wherein the support is a stretcher wherein the patient lies face down on said stretcher.

3. The device according to claim 1, wherein said at least one transparent window is made from a transparent material.

4. The device according to claim 3, wherein the at least one transparent window presents flat and parallel upper and bottom surfaces.

5. The device according to claim 4, wherein the at least one transparent window is made of glass or a transparent polymer.

6. The device according to claim 1, wherein light-regulating means are placed below the at least one window and mounted to the support.

7. The device according to claim 6, wherein the light-regulating means comprise a diaphragm.

8. The device according to claim 1, wherein said at least two laser-light producing means produce laser lights of different wavelengths.

9. The device according to claim 8, wherein two laser light producers are placed so that the beams produced are perpendicular to one another.

10. The device according to claim 9, wherein a beam divider is placed so that said beams perpendicular to one another incide collinearly on the light-directing means.

11. The device according to claim 1, wherein light-intensity regulating means for regulating the intensity of laser light beams are placed in front of each of the at least two laser-light producing means.

12. The device according to claim 11, wherein the light-intensity regulating means comprise a variable attenuator.

13. The device according to claim 1, wherein the light-directing means comprise a galvanometric scanner.

14. The device according to claim 1, wherein the at least one wavelength filter is an interferometric filter.

15. The device according to claim 1, wherein the light-sensing and imaging means comprise a CCD camera, said camera utilizing a CCD sensor with enhanced sensitivity to light in the near infrared portion of the spectrum.

16. The device according to claim 15, wherein the CCD camera is a 2D CCD camera.

17. The device according to claim 1, wherein a cover for isolating ambient light is disposed between the at least one transparent window and the light-sensing means.

18. The device according to claim 15, wherein said CCD camera incorporates an optic which allows measuring lighting intensity of the full 2D surface of the breast as a single photograph of the NIR light reflected by each position of the laser light beam, allowing that a complete area of interest is measured in only one take per laser position;

wherein said CCD camera enables taking multiple images of each position in succession so as to improve the dynamic range with a high dynamic range (HDR) algorithm and improves the signal-noise ratio; and wherein said CCD camera makes up for the position and the size of the breast resting on the transparent window.

* * * * *